United States Patent [19]

Styles

[11] Patent Number: 5,383,598

[45] Date of Patent: Jan. 24, 1995

[54] AIR FRESHENER RETAINER

[76] Inventor: Robert L. Styles, 606 William Ave., Colorado Springs, Colo. 80906

[21] Appl. No.: 188,043

[22] Filed: Jan. 27, 1994

[51] Int. Cl.⁶ .............................................. A61L 9/12
[52] U.S. Cl. ........................................ 239/57; 239/34
[58] Field of Search .......................... 239/34, 53–60; 223/86

[56] References Cited

U.S. PATENT DOCUMENTS

| | | | |
|---|---|---|---|
| 1,491,407 | 4/1924 | Jordan | 239/57 |
| 1,496,326 | 6/1924 | Schulte | 239/57 |
| 1,758,347 | 5/1930 | Beibin | 239/60 |
| 1,769,409 | 7/1930 | Armstrong | 239/57 |
| 2,734,769 | 2/1956 | Holz | 239/57 |
| 2,755,954 | 7/1956 | Antritter | 239/57 |
| 3,065,915 | 11/1962 | Samann | 239/58 |

*Primary Examiner*—Karen B. Merritt
*Attorney, Agent, or Firm*—Richard W. Hanes

[57] ABSTRACT

An isolation retainer for chemically treated aromatically emissive substances, comprising a pair of opposing side members attached together along their respective perimeters to form a pocket therebetween for the retention of the chemically treated aromatically emissive substance, where the side members contain one or more apertures for providing air flow through the side member and into the interior of the pocket to allow the escape of the aromatic vapors emitting from the chemically treated substance, and an elongated aperture disposed in the perimeter of the retainer for inserting the aromatically emissive substance into the pocket.

1 Claim, 1 Drawing Sheet

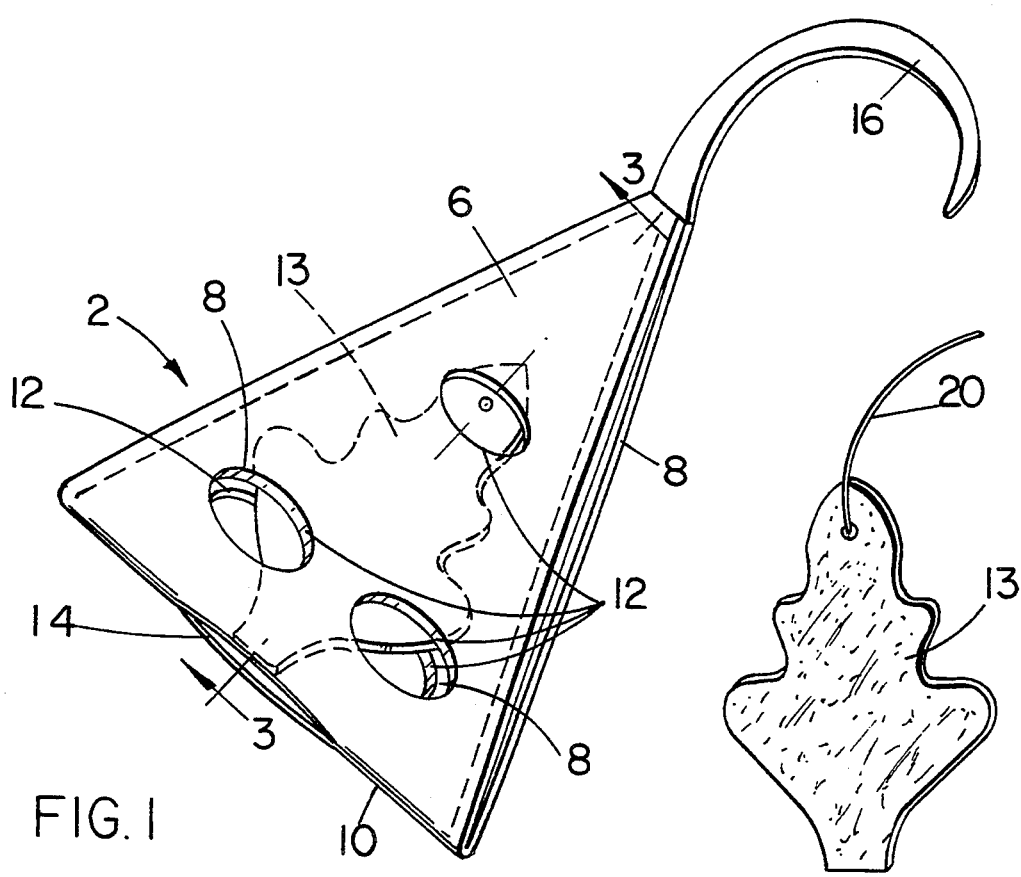
FIG. 1
FIG. 2
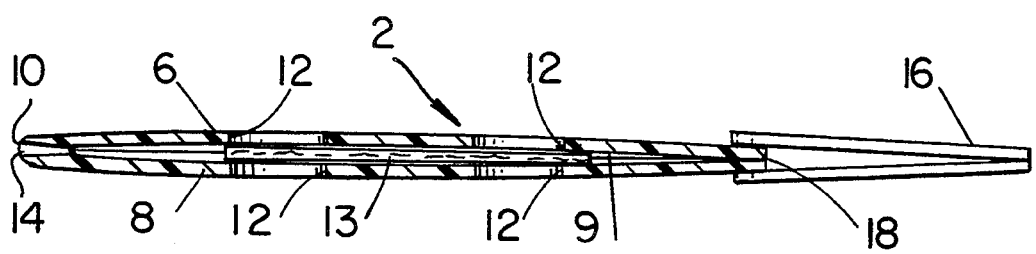
FIG. 3

AIR FRESHENER RETAINER

The present invention relates to a pocket type retainer for suspending and isolating chemically treated materials.

BACKGROUND OF THE INVENTION

The aromatic emissions of certain chemically treated absorbent material are often used as home, commercial or industrial air fresheners, deodorants, insect repellant or for new flagrance creation. Such products are often designed to be hung or suspended in a room, automobile, aircraft, on a patio, porch or deck. Several difficulties and problems arise however when the chemically treated objects are suspended with the hanging means and protective packaging with which most of them are originally supplied. For example, when suspended by the typically supplied elastic cord, the chemically treated object may inadvertently come into contact with walls, upholstery, draperies or other furnishings and if left in such contact for a period of time the resident chemical compounds in the product will discolor or stain the surface or object with which it has remained in contact.

Many of the air freshener and similar products are packaged for sale in sealed plastic bags or containers. Their instructions for use often suggest that the plastic container be cut and only partially removed or pulled down and away from the product in order to expose only a part of the product to the surrounding air. As the exposed portion of the freshener looses its potency, an additional portion of it is to be exposed by pulling the plastic bag further down and away. In addition to exposing only small potions of the freshener device at a time, in order to conserve its effectiveness, such a technique also serves to control the strength of the chemical or aromatic emissions which are released. With the device of the present invention, this rather crude prior method of controlling the life, strength and effectiveness of such an object, is eliminated.

Accordingly, the primary object of the present invention is to provide a protective covering for any type of chemically treated substance where air contact with the substance is essential to its proper operation and function.

A second object of the invention is to provide a ventilated housing for aromatic or chemically emissive substances which housing may also serve as the means to suspend the substance in the area to which it is to be effective.

Another object of the invention is to provide a housing for aromatic or chemically emissive devices which will control the degree of exposure of the contained chemical materials to the air, extending the life of the device and creating an even distribution of the emissions therefrom, while at the same time eliminating the unsightly appearance of a plastic packaging bag hanging around the product.

A still further object of the invention is to eliminate the need for costly decoration, design and coloring of air freshener products, such design being unnecessary because the freshener will, in use, be contained in the more elaborately designed and permanent type of container of the present invention.

A further object of the invention is to provide a housing for aromatic products where the they can be frequently changed to provide a variety of fragrances, while at the same time maintaining the decor of the housing of the present invention.

Other and further objects, features and advantages of the invention will become apparent upon a reading of the following detailed description of a preferred form of the invention, taken in conjunction with the accompanying drawings in which:

FIG. 1, is a perspective view of one embodiment of the invention showing the chemically treated air freshener object which is enclosed therein in dotted lines.

FIG. 2 is a side elevational view of the air freshener object which is intended to be housed in the retainer of the present invention.

FIG. 3 is a cross sectional view taken along line 3—3 of FIG. 1.

DETAILED DESCRIPTION

The air freshener housing 2 of the present invention includes a pair of opposing matched side members 6 and 8 of any desired shape, the perimeters of which are sewn or attached together so as to form a pocket or pouch 9 between the two members. The side members 6 and 8 may be formed of a single piece of pliable material which is folded over on itself so that the fold 10 constitutes one of the perimetrical edges of the pouch, as shown in the drawings of the preferred form of the invention. The material of which the pouch sides are made can be of any composition as long as the material does not itself absorb the chemical from the air freshener object 13. The material of the pouch must be such as to separate the chemicals of the air freshener object from possible abutting or contacting surfaces or objects so as to prevent the transfer of the chemicals to the abutting surfaces or objects with resultant stain. discoloration and consignment of odor.

Each of the sides 6 and 8 of the pouch are provided with one or more apertures 12 to provide the ventilation necessary to release the fragrance of the air freshener object 13 retained within the pouch 9. Although three large apertures are shown in the drawing of a preferred form of the invention, it should be made clear that the apertures can vary from a plurality of pin sized holes to the larger apertures, as shown. The size and number of holes in the sides of the pouch are fundamental to the regulation of exposure to the air and the resultant life of the air freshener device housed inside and also in controlling the strength or character of the aromatic emissions. Along one edge seam or along the fold 10 there is provided a slot 14 to accommodate the insertion into the pouch 9 of the air freshener object 13.

The pouch is provided with a hanging strap 16 attached to the sides of the pouch for suspending the assembly from a handle, hook, curtain rod or the like. In place of the strap 16, or in addition to it, the edge of the pouch can be provided with an aperture 18 through which the hanger cord 20 of the air freshener object 13 can be trained so that the whole assembly can be suspended by the air freshener's hanging cord, with the pouch acting only as a protective ventilation covering.

I claim:

1. An isolation retainer for aromatically emissive substances, comprising;
    a pair of opposing side members attached together along their respective perimeters to form a pocket therebetween for the retention of a chemically treated aromatically emissive substance where at least one of the side members contains at least one aperture for providing air flow through the said side member and into the interior of the pocket;

an elongated aperture disposed in the perimeter of the retainer for inserting the aromatically emissive substance into the said pocket; and second aperture means for providing access through which a hanger which is attached to the emissive substance may be passed.

* * * * *